United States Patent [19]

Markle et al.

[11] Patent Number: 5,357,732
[45] Date of Patent: Oct. 25, 1994

[54] METHOD FOR ASSEMBLING PACKAGE FOR AN ACTIVE MEDICAL DEVICE

[75] Inventors: David R. Markle, Paoli, Pa.; Stuart P. Hendry, Bierton; Michael P. Irvine, Watlington, both of United Kingdom

[73] Assignee: Biomedical Sensors, Ltd., High Wycombe, England

[21] Appl. No.: 64,615

[22] Filed: May 20, 1993

Related U.S. Application Data

[62] Division of Ser. No. 888,569, May 22, 1992, Pat. No. 5,246,109.

[51] Int. Cl.5 .............. B65B 31/02; B65B 5/08; B65B 61/00
[52] U.S. Cl. ................... 53/410; 53/425; 53/453; 53/471; 53/474
[58] Field of Search .......... 53/410, 425, 428, 453, 53/471, 472, 474; 206/328, 439, 471

[56] References Cited

U.S. PATENT DOCUMENTS

| | | | |
|---|---|---|---|
| 31,879 | 5/1885 | Lübbers et al. | 436/133 |
| 3,011,293 | 12/1961 | Rado | 53/410 |
| 3,909,504 | 9/1975 | Browne | 53/472 X |
| 3,930,850 | 1/1976 | Bazell et al. | 206/439 |
| 4,200,110 | 4/1980 | Peterson et al. | 128/634 |
| 4,528,616 | 7/1985 | Koppensteiner | 206/328 X |
| 4,941,308 | 7/1990 | Grabenkort et al. | 53/425 |
| 4,946,038 | 8/1990 | Eaton | 53/410 X |
| 5,047,208 | 9/1991 | Schweitzer et al. | 422/58 |
| 5,082,112 | 1/1992 | Dunklee | 206/471 X |
| 5,178,267 | 1/1993 | Grabenkort et al. | 53/425 X |

*Primary Examiner*—Horace M. Culver
*Attorney, Agent, or Firm*—Peter C. Richardson; Lawrence C. Akers; Mark Dryer

[57] ABSTRACT

A method for assembling a package for an active medical device which comprises making an opening in a wall of a recess shaped to receive the device, placing a gasket against the wall and about a band mounted through a flat portion of the wall, inserting the band through the opening so the gasket is flush against the wall, installing an outer part about the band to hold the gasket against the wall to form a sterile barrier, and placing a lid over the recess to contain the device within a sterile field.

3 Claims, 5 Drawing Sheets

METHOD FOR ASSEMBLING PACKAGE FOR AN ACTIVE MEDICAL DEVICE

This application is a divisional of application Ser. No. 07/888,569, filed on May 22, 1992 (now U.S. Pat. No. 5,246,109).

FIELD OF THE INVENTION

This invention relates to a package for an active medical device and the method of assembly and testing thereof. More particularly, a structure that contains the active medical device yet, allows testing without compromise of the sterile barrier provided by the package.

BACKGROUND OF THE DISCLOSURE

Described herein are a package for the active medical devices and methods of manufacture and/or use not found in the literature or practiced in the field. The literature is of interest for its teachings of the knowledge of skilled artisans at the time of this invention of the package for the active medical device and method of assembly and testing thereof.

Disposable medical devices are sold in groups of like size and type which are typically carried in an over carton in a dozen or more individually packaged, identical devices- A package can be removed from the over carton and opened to obtain a single disposable device. Individual packaging maintains a sterile barrier for each disposable medical device. Consequently, the package for each should be inexpensive, easy to open without contamination of the product and structurally adequate to protect the sterility of the product prior to use.

Commonly used packaging for disposable medical devices includes two components; a flat top or cover with printed product information as, for example, product size, type, name of manufacturer, instructions and the like. The top or cover is usually a thin sheet of extrusion coated paper having a polyethylene layer and a heat sealable lacquer layer. The paper is called Tyvek paper and the polyethylene is added for tear resistance.

The other or second component of the often used package is a drawn semi rigid tub which has a recess for receiving the product and a flange for supporting the top or cover. The tub is thermal formed from semi rigid polymer sheet which is heated and drawn such that the depth of the recess is no more than one and one-half times the width. Products which are wider than they are deep have to be packed sideways, or the package has to be drawn less than required for efficient use of the drawn polystyrene material. Typically, the flange is the thickest part of the formed tub in that it is not drawn and the corners of the recess are the thinnest area because they are stretched the most. A ratio of flange thickness to corner thickness of six to one is about the maximum amount of thinning that can be accomplished with an economical starting thickness for the polymer sheet. The flange protects the device and provides support during opening.

The cover and tub flange are heat sealed to securely enclose the product within the recess of the tub, but a portion along an edge is usually left unsealed in order to provide an area where the top can be peeled from the flange. In particular, the unsealed portion of the edge of the top can be fanned away from the edge of the flange and then grasped and peeled away from the heat sealed areas about the rest of the flange. The product remaining within the recess is supported thereby during peeling. After removal of the top or cover, the product can be accessed without having violated the sterile field of the product, but the use of gloved hands is necessary to maintain sterility. Since the product and package are typically sterilized after assembly but before use, the package has to remain a barrier to microbes and the like until the described opening procedure is performed.

Active medical device may include optical fibers or fiber optic chemical sensors used in vivo as probes; such devices must be sensitive to slight changes in gas or ion concentrations. U.S. Pat. No. 4,200,110 has a fiber optic probe with an ion permeable membrane enclosure about the distal ends of a pair of fiber optics. Change in color of a pH sensitive dye is detected. U.S. patent reissue 31,879 has a method for measuring concentration of an analyte in a sample that changes color and/or the intensity of light emitted from a fluorescent indicator attached to the fiber. U.S. Pat. No. 5,047,208 has an optical sensor for blood gas measurement with a pH sensitive absorption dye between the end of the fiber and a mirror, The mirror is located by a tube which carries a mirror spaced from and coaxially aligned with the fiber so the dye can be in the space, These and other patents are typical of the microscopic constructions required for in vivo blood analysis and the manner in which structures have been made, Blood gas sensors are typically packaged in a vessel filled with solution and then sealed in a sterility protecting package as described, The solution maintains the chemicals of the sensor fresh and ready to be used, Optic and electrical signals may be transmitted and returned through miniature conductors pass through a lumen of the blood sensor catheter during use in vivo, The ability to access those miniature conductors before delivery to verify that the sensors are viable and may be used reliably is important to the manner in which active medical devices are handled in their distribution and ultimate application.

SUMMARY OF THE INVENTION

A package for an active medical device with its conductors between the distal and proximal ends thereof preferably has a film member having a pocket formed therein to define a recess shaped to receive the active medical device, The film member includes a flange in a plane about the recess and a wall of the recess is most preferably formed as part of the pocket, The wall includes at least a flat portion generally perpendicular to the plane of the flange.

An opening is preferably in the flat portion for providing access from the recess to the outside of the pocket. A lid may cover the recess of the pocket and enclose the active medical device. The lid is most preferably associated with the flange of the film member and thereby contains the active medical device within a sterile field in the recess therein. A connection may in the preferred embodiment be mounted through the flat portion of the wall of the pocket to assure the sterile field within the lidded recess. An inner part and an outer part which conjugate over the opening to seal the opening and insure sterility within the recess is the junction of the preferred embodiment. The junction preferably includes test means for the conductors of the medical device so that electrical and optical transmissions may pass through the junction without removal of the lid or breach of the sterile field. The inner part may have a central web therein as part of the test means so the active medical device can fit thereto in position to transmit optical signals from light conductors. The central web most preferably has thereabout a plurality of spaced apart electrically conductive pins as another part of the test means which distally couple with the test linkage proximally received. A window of transparent material in the central web permits optical signal transmission therethrough.

The inner part includes preferably a band with a brim thereabout so the band fits through the opening and the brim faces the wall about the opening. The outer part may include a collar with a rim thereabout so the collar conjugates with the band of the inner part that extends through the opening and the rim abuts in tight facing relation the wall about the opening. The brim most preferably joins the band to support a gasket thereabout and the gasket may be of a resilient material for compression between the wall and the brim when the inner and outer parts are conjugate.

Threads about the band of the inner part that extends through the opening may in the preferred embodiment mate with complimentary threads on the collar of the outer part so that the inner and outer parts may be drawn axially together to compress the gasket against the wall.

A method of assembly of the package and the junction including the steps of making an opening in the wall of a recess in a package, placing a gasket against a brim and about a band of an inner part of the junction, inserting the band through the opening in the wall so the gasket is flush against the wall, and installing an outer part coaxially about the band whereat it extends beyond the opening to hold the gasket tightly against the wall to form a sterile barrier. The added step of threading a collar onto the extended band to secure the outer and inner parts may be included.

A method of testing an active medical device in a package that provides a sterile barrier by means of the junction including the steps of inserting the active medical device in a recess within the package, attaching the active medical device to the junction for transmission of signals in and out of the package through the junction, applying signals of light and electric energies to the junction from outside the package, and receiving a modified signal from the active medical device through the junction.

DETAILED DESCRIPTION OF THE INVENTION

A package 10 for an active medical device 11 and methods of assembly and testing are disclosed and claimed. The claims are not limited to the structure for the package 10 for the active medical device 11 described and illustrated by way of example and the methods of assembly and testing specifically explained. The claims are to be considered in view of the existing knowledge of skilled artisans in this field prior to the inventions defined by the language of the claims herein as amended or considered in view of that knowledge of skilled artisans.

Figure 1:
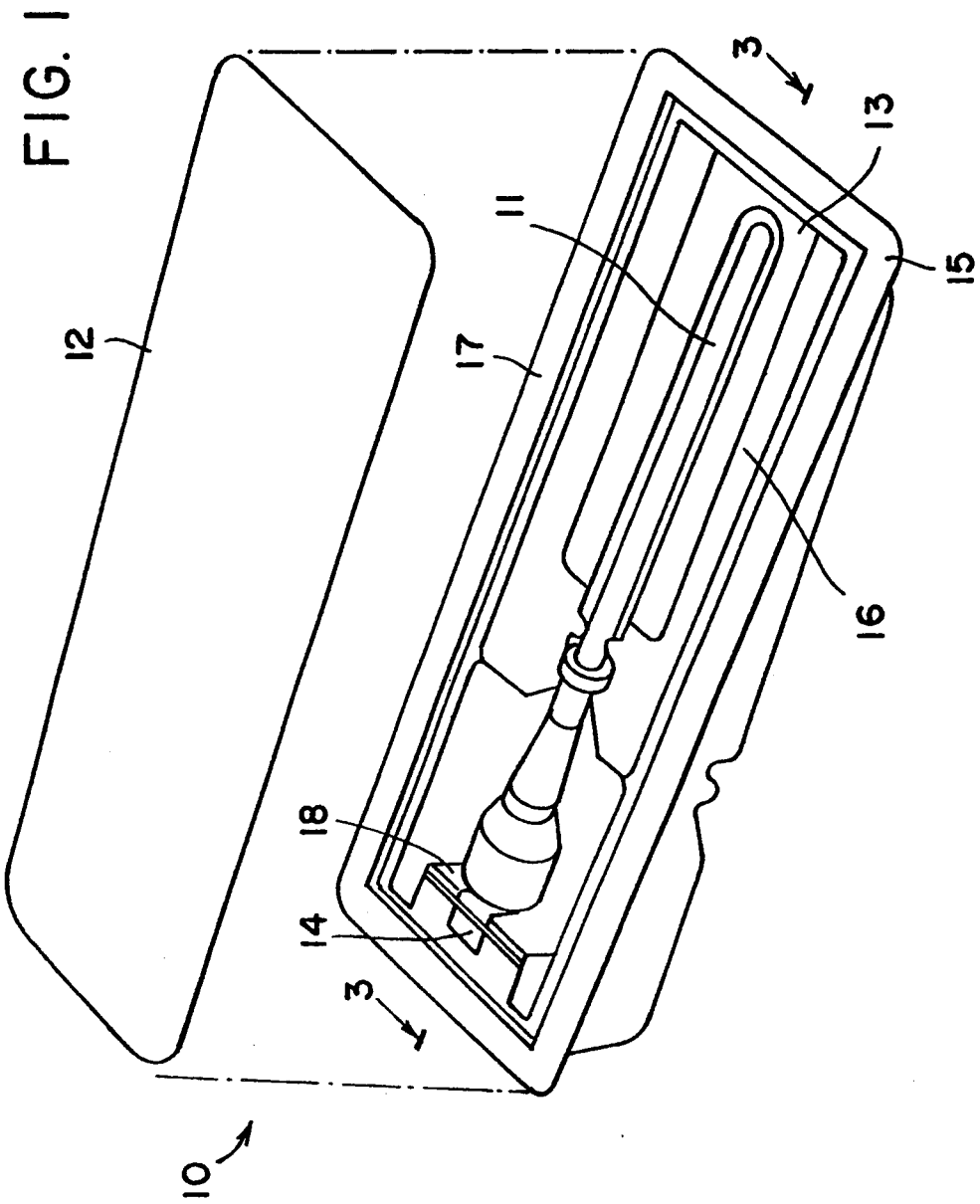
FIG. 1 is a perspective view of the package pocket showing the lid removed above the recess thereof for clarity of the illustration of the active medical device in its packed position before use and connected for testing.

The package 10 for the active medical device 11 with its conductors between the distal and proximal ends and thereof is shown in FIG. 1, a perspective view of the package 10 with a lid 12 positioned above a recess 13 thereof. As used herein the terms distal and proximal are with respect to the leading end of the active medical device 11, i.e. the part that enters the patient; this is common usage in the medical field. The active medical device 11 is depicted in its packed position before use and is attached to a junction 14 ready for testing. Skilled artisans will appreciate that the lid 12 will maintain a sterile field within the package 10 and about the active medical device 11. While the active medical device 11 is in a preferred embodiment a blood gas sensing catheter, the active medical device 11 need not be medical and the package 10 need not be sterile. For example, any device could have an active component and the packaging could be sealed for cleanliness, e.g. a semiconductor in a dust free environment within the packaging.

The package 10 disclosed in FIG. 1 has a film member 15 having a pocket 16 formed therein to define the recess 13 shaped to receive the active medical device 11. The film member 15 is a polymer sheet that has been vacuumed formed with heat and pressure. The preferred material is a semi rigid and transparent sheet of plastic less than 1 mm. thick. The film member 15 includes a flange 17 in a plane about the recess 13 and a wall 18 of the recess 13 is most preferably formed as part of the pocket 16. The wall 18 includes at least a flat portion 19 generally perpendicular to the plane of the flange 17.

Figure 3:
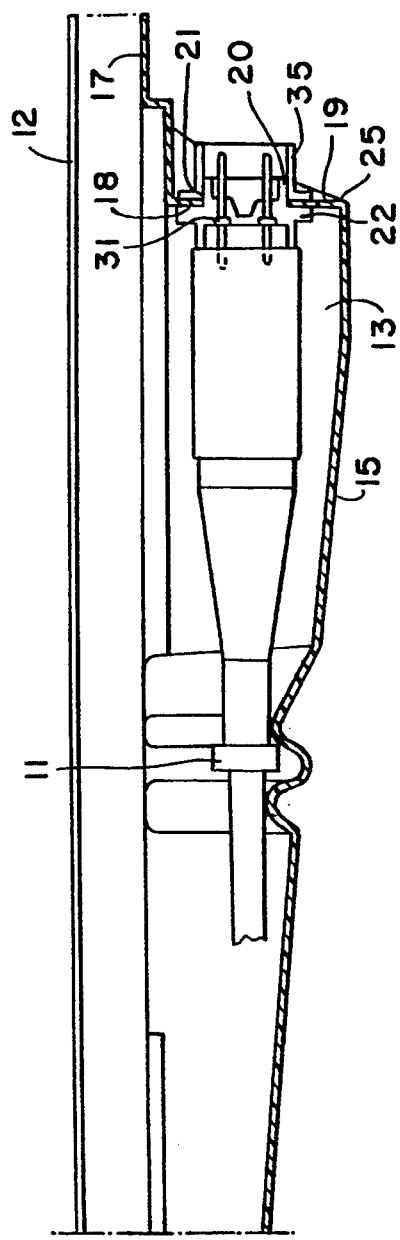
FIG. 3 is a partial side view in cross section of the package and the active medical device of FIG. 1 as would be seen if the cross section were taken along line 3—3 in FIG. 1.

An opening 20 is preferably D shaped with a straight edge 21 and is punched or cut into the flat portion 19 for providing access from the recess 13 to the outside of the pocket 16, see FIG. 3. The lid 12 covers the recess 13 of the pocket 16 and encloses the active medical device 11. The lid 12 is most preferably gas permeable for use with gas sterilization and Tyvek material is typically used. The lid 12 is associated with the flange 17 of the film member 15 by heat or solvent activated adhesive to thereby seal and contain the active medical device 11 within a sterile field in the recess 13 therein.

Figure 2:
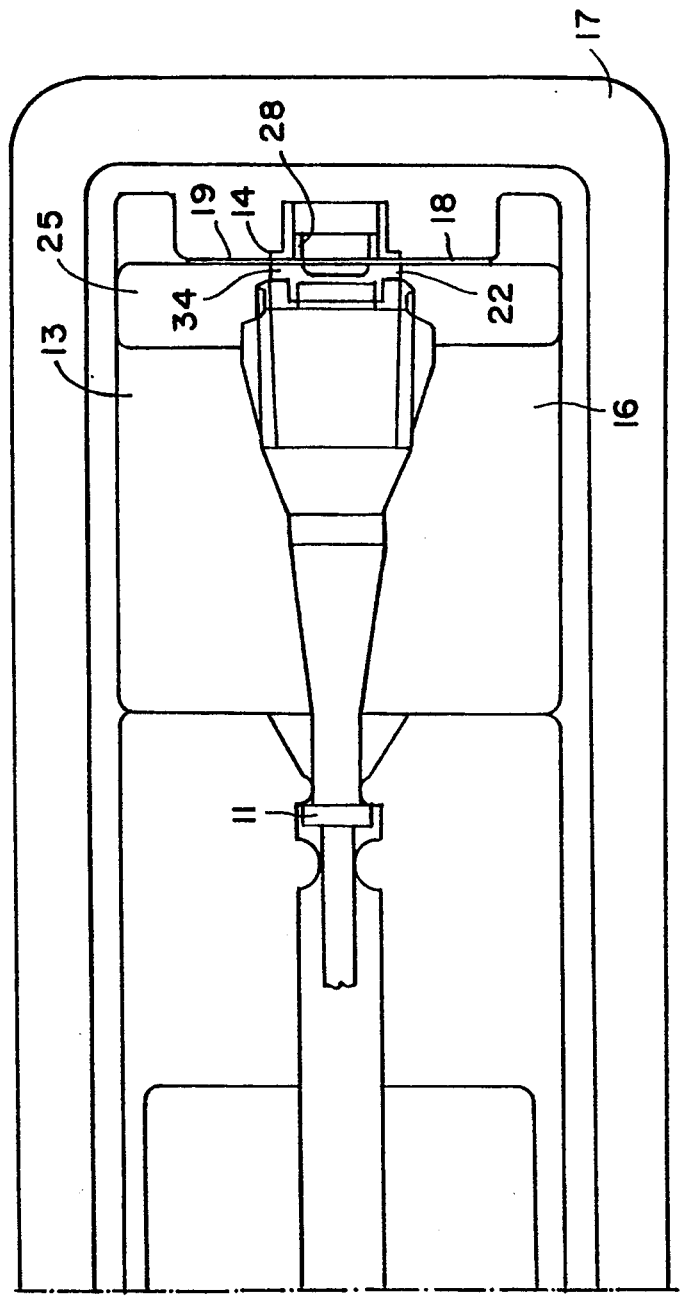
FIG. 2 is a partial top view of package for the active medical device of FIG. 1 as would be seen if the lid were completely removed.

The disclosure herein is related to that of commonly assigned patent application Ser. No. 07/887,986, filed May 22, 1992 and entitled "BARRIER FOR A CONNECTOR" (now U.S. Pat. No. 5,230,031). The disclosure of that other application is incorporated herein and made a part hereof by reference and it describes and shows a particular connector for an in vivo blood gas sensing catheter. The preferred embodiment of the present package 10 is designed to receive one side of that connector that in vivo blood gas sensing catheter has optic fibers and electrical conductors that terminate proximally in its connector which can be attached to monitoring instrumentation or in the situation disclosed and explained herein the package 10. Consequently, the proximal end of that connector of that in vivo blood gas sensing catheter is attached to the inside portion of the junction 14 in the package 10 as shown in FIGS. 1, 2 and 3. The junction 14 permits the transmission of optical and electrical signals even though the package 10 is sealed and the sterile field therewithin has not been breached.

Specifically, the connector described in the reference has a conjugating part with terminal face features and is keyed to align the terminal face features. The terminal face features include conductors for electrical circuits and optical paths in the in vivo blood gas sensing catheter. A connection 22 occurs between the conjugating part and the junction 14 herein when the active medical device 11 of the preferred embodiment is packaged has the features fully conjugated.

Figure 4:
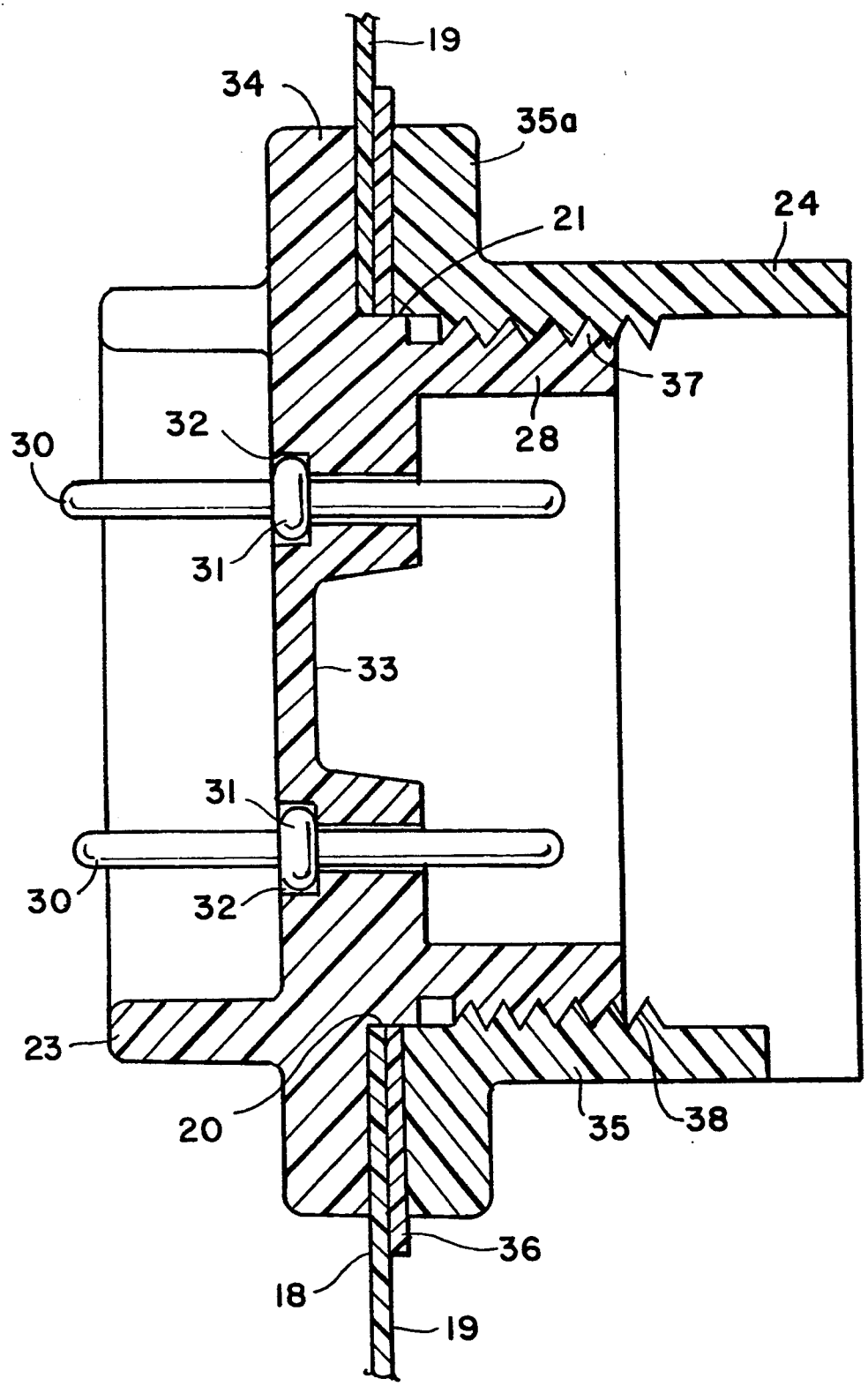
FIG. 4 is an enlarged view in cross section of the portion of the package similar to FIG. 3 and showing the detail of the junction for the active medical device passage through an opening in a wall of the package.

The junction 14 is in the preferred embodiment mounted through the flat portion 19 of the wall 18 of the pocket 16 to assure the sterile field within the lidded recess 13. FIG. 2 is a partial top view of package 10 for the active medical device 11 of FIG. 1 as would be seen if the lid 12 were completely removed. FIG. 3 is a partial side view in cross section of package 10 and the active medical device 11 of FIG. 1 as would be seen if the cross section were taken along line 3—3 in FIG. 1. The positioning of the connector conjugating part is shown as it would appear in the preferred embodiment if the active medical device 11 were attached to the junction 14. FIG. 4 is an enlarged view in cross section of the portion 19 of the package 10 and is similar to FIG. 3 in the showing of the details of the junction 14 for the active medical device 11 where the junction 14 passes through the opening 20 in the wall 18 of the package 10, as seen in FIG. 4.

Figure 5:
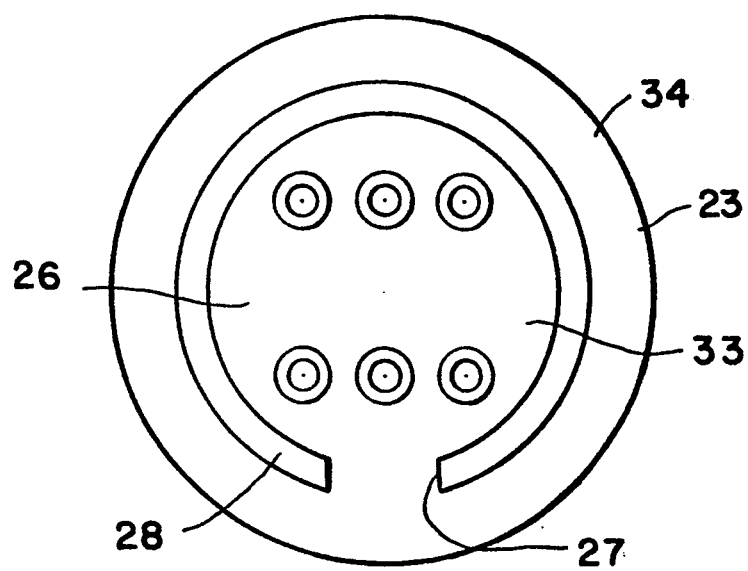
FIG. 5 is an enlarged distal end view of the inner part of the junction as would be seen from inside the package.
Figure 6:
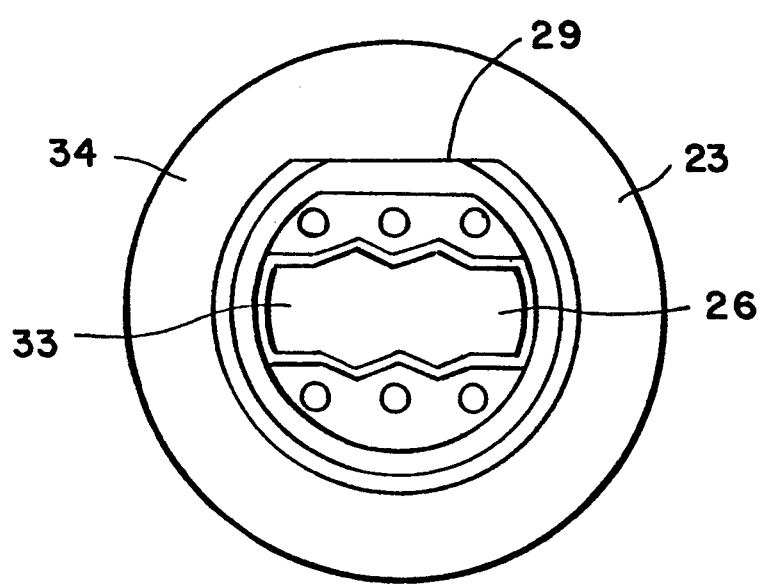
FIG. 6 is an enlarged proximal end view of the inner part of the junction or the side that faces the wall of the package.

An inner part 23 and an outer part 24 conjugate over the opening 20 to seal the opening 20 and insure sterility within the recess 13. The inner and outer parts 23 and 24 are molded rigid transparent polymer and form the preferred embodiment of the junction 14. The junction 14 preferably includes test means 25 for the conductors of the active medical device 11 so that electrical and optical transmissions may pass through the junction 14 without removal of the lid 12 or breach of the sterile field. Specifically and as shown in FIG. 5, an enlarged distal end view of the inner part 23 of the junction 14 as would be seen from inside the package 10, and FIG. 6, an enlarged proximal end view of the inner part 23 of the junction 14 or the side that faces the wall 18 of the package 10, the inner part 23 may have a central web 26 therein as part of the test means 25 so the active medical device 11 can fit thereto in position to transmit optical signals from light conductors. In FIG. 5 a bottom slot 27 is provided on the band 28 distally to receive the key of the conjugating part and as used herein bottom is with reference to the package 10 as shown in the Figures, particularly FIG. 1. In FIG. 6 a section 29 of the band 28 facing proximally is removed to position the band 28 relative to the opening 20 straight edge 21. The central web 26 has thereabout a plurality of spaced apart electrically conductive pins 30 as another part of the test means 25 which distally couple with the test linkage proximally received. The preferred plurality of spaced apart electrically conductive pins 30 are conductive metal such as brass, bronze tin plated, silver plated or gold plated; specifically, part number 1364H as made and sold by Prestincert Fasteners Division of Belling Lee Limited of Middlesex, England. In the inner part 23 there are six spaced apart electrically conductive pins 30 that are parallel to one another with three above and three below the central web 26, as shown in FIGS. 4, 5 and 6. The spaced apart electrically conductive pins 30 are best seen in side cross section 29 in the enlarged view of FIG. 4 wherein an enlarged center bead 31 sits in a counter sunk hole 32 in inner part 23 and is held therein by heat staking, glue or press fit as desired for assembly ease.

A window 33 of transparent material is located in the central web 26 to permit optical signal transmission therethrough. The inner part 23 includes the band 28 with a brim 34 thereabout so the band 28 fits through the opening 20 and the brim 34 faces the wall 18 about the opening 20 as seen in FIG. 4. The outer part 24 may include a collar 35 with a rim 35a thereabout so the collar 35 conjugates with the band 28 of the inner part 23 that extends through the opening 20 and the rim 35a abuts in tight facing relation to the wall 18 about the opening 20 also in FIG. 4. The brim 34 most preferably joins the band 28 to support a gasket 36 thereabout and the gasket 36 may be of a resilient material, such as soft silicone rubber, for compression between the wall 18 and the outer part 24 when the inner and outer parts 23 and 24 are conjugate.

Figure 7:
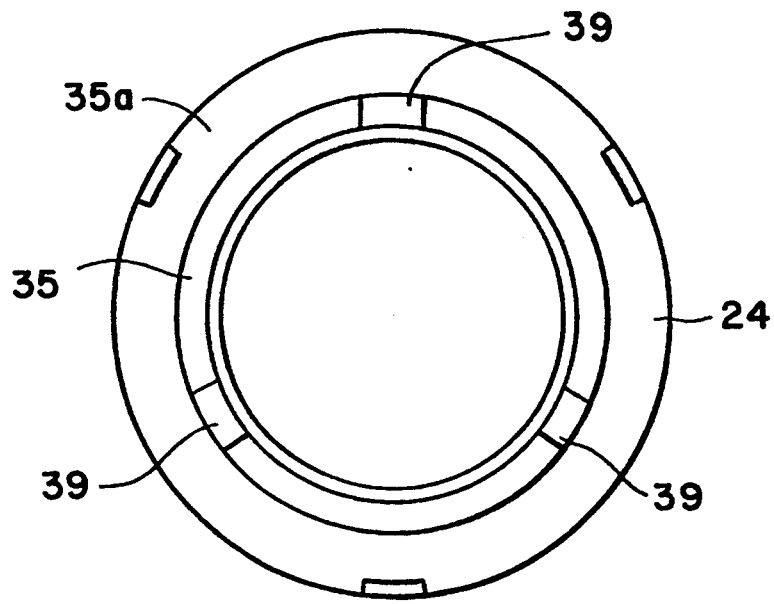
FIG. 7 is an enlarged proximal end view of the outer part of the junction as would be seen from outside the package.
Figure 8:
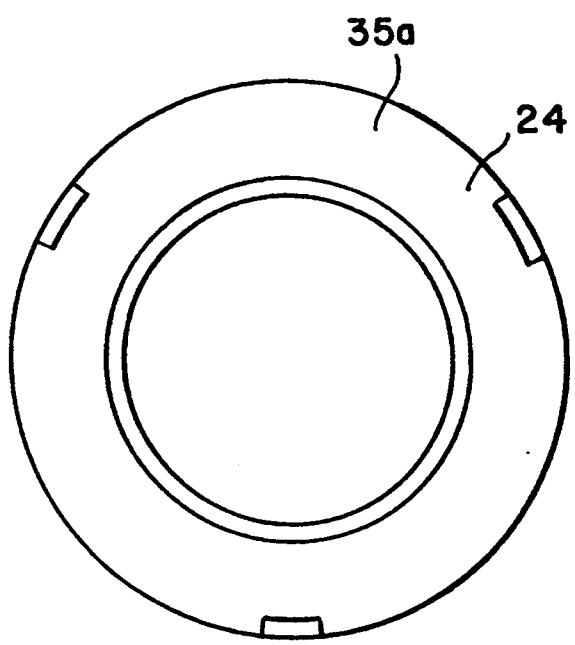
FIG. 8 is an enlarged distal end view of the outer part of the junction or the side that abuts the wall of the package.

Threads 37 about the band 28 of the inner part 23 that extends through the opening 20 may in the preferred embodiment mate with complimentary threads 38 on the collar 35 of the outer part 24 so that the inner and outer parts 23 and 24 may be drawn axially together to compress the gasket 36 against the wall 18, as in FIG. 4. Adhesive or high frequency welding can be used to secure the threaded joint between the inner and outer parts 23 and 24. FIG. 7 is an enlarged proximal end view of the outer part 24 of the junction 14 as would be seen from outside the package 10. There are three notches 39 shown in FIG. 7, spaced about the collar 35 and are useful with a spanner tool when compressing the gasket 36 by tightening the threads 37 and 38 between the collar 35 and band 28. FIG. 8 is an enlarged distal end view of the outer part 24 of the junction 14 showing the side that abuts the wall 18 of the package 10.

A method of assembly of the package 10 and the junction 14 including the steps of making the opening 20 in the wall 18 of the recess 13 in the package 10, inserting the band 28 through the opening 20 in the wall 18, placing the gasket 36 against the wall 18 and about the band 28 of the inner part 23 of the junction 14 so the gasket 36 is flush against the wall 18, and installing the outer part 24 coaxially about the band 28 whereat it extends beyond the opening 20 to hold the gasket 36 tightly against the wall 18 to form a sterile barrier. The added step of threading the collar 35 onto the extended band 28 to secure the inner and outer parts 23 and 24 may be included.

A method of testing the active medical device 11 in the package 10 that provides a sterile barrier by means of the junction 14 including the steps of inserting the active medical device 11 into the recess 13 within the package 10, attaching the active medical device 11 to the junction 14 for thereafter allowing transmission of signals into and out of the package 10 through the junction 14, applying signals of light and electric energies to the junction 14 from outside the package 10, and receiving modified signals from the active medical device 11 through the junction 14.

What is claimed is:

1. A method for assembling a package containing an active medical device having sensors comprising the following steps:

making an opening in a wall of a recess defined by a film member, which recess is shaped to receive the active medical device;

inserting the active medical device in the recess;

inserting through the opening in the wall a band of an inner part of a junction mounted through a flat portion of the wall;

placing a gasket against the wall and about the band so the gasket is flush against the wall;

installing an outer part coaxially about the band whereat it extends beyond the opening to hold the gasket tightly against the wall to form a sterile barrier; and placing a lid against a flange of the film member to cover the recess and thereby contain the active medical device within a sterile field in the recess.

2. A method according to claim 1 in which the outer part includes a threaded collar which is threaded onto the extended band to secure outer and inner junction parts.

3. A method according to claim 1, in which test means adapted to allow the passage of electrical and optical signals is included in the junction so that the sensors of the medical device may be tested without breach of the sterile field.

* * * * *